(12) United States Patent
Shemwell et al.

(10) Patent No.: US 10,080,597 B2
(45) Date of Patent: Sep. 25, 2018

(54) INTRAMEDULLARY ANCHOR FOR INTERPHALANGEAL ARTHRODESIS

(71) Applicant: Wright Medical Technology, Inc., Memphis, TN (US)

(72) Inventors: Jessica L. Shemwell, Millington, TN (US); Pearce Branthover, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 0 days.

(21) Appl. No.: 14/420,260

(22) PCT Filed: Dec. 19, 2014

(86) PCT No.: PCT/US2014/071526

§ 371 (c)(1),
(2) Date: Feb. 6, 2015

(87) PCT Pub. No.: WO2016/099550

PCT Pub. Date: Jun. 23, 2016

(65) Prior Publication Data

US 2016/0338747 A1    Nov. 24, 2016

(51) Int. Cl.
*A61B 17/72* (2006.01)
*A61B 17/68* (2006.01)
*A61F 2/42* (2006.01)

(52) U.S. Cl.
CPC ...... *A61B 17/7291* (2013.01); *A61B 17/7233* (2013.01); *A61B 17/7283* (2013.01); *A61B 2017/681* (2013.01); *A61F 2002/4228* (2013.01)

(58) Field of Classification Search
CPC ............ A61B 17/7291; A61B 17/7233; A61B 17/7283; A61B 17/725; A61F 2002/4228
See application file for complete search history.

(56) References Cited

U.S. PATENT DOCUMENTS 321,389 A    6/1885    Schirmer
346,148 A    7/1886    Durham
(Continued)

FOREIGN PATENT DOCUMENTS

CN    1047025 A    11/1990
CN    201085677    7/2008
(Continued)

OTHER PUBLICATIONS

Brochure MKT 016 A: iFuse HT Hammertoe Correction Implant, OrthoPro LLC, 2 pages, undated.
(Continued)

*Primary Examiner* — Jacqueline Johanas
(74) *Attorney, Agent, or Firm* — Duane Morris LLP

(57) ABSTRACT

An intramedullary implant has opposite ends inserted into bores in abutting phalanges for correcting hammer toe and for similar arthrodesis procedures. A rear end of the implant may be threaded and is received in a bore in the proximal phalanx. A front end has an asymmetric pointed shape with longitudinally and/or angularly spaced rear-facing gripping flukes. The pointed front end is received in the middle phalanx. The asymmetric pointed shape is self-aligning, enabling entry to begin without first longitudinally aligning the bones. The rear end when screwed into place can be rotated to select the orientation of the asymmetric pointed shape. The pointed front end is inserted and pushed to bring the phalanges into abutment where the implant holds them against retraction or rotational displacement.

12 Claims, 4 Drawing Sheets

(56) References Cited

U.S. PATENT DOCUMENTS

| | | |
|---|---|---|
| 348,589 A | 9/1886 | Sloan |
| 373,074 A | 11/1887 | Jones |
| 430,236 A | 6/1890 | Rogers |
| 561,968 A | 6/1896 | Coulon |
| 736,121 A | 8/1903 | Lipscomb |
| 821,025 A | 5/1906 | Davies |
| 882,937 A | 3/1908 | Pegley |
| 1,966,835 A | 7/1934 | Stites |
| 2,140,749 A | 12/1938 | Kaplan |
| 2,361,107 A | 10/1944 | Johnson |
| 2,451,747 A | 10/1948 | Kindt |
| 2,490,364 A | 12/1949 | Livingston |
| 2,600,517 A | 6/1952 | Rushing |
| 2,697,370 A | 12/1954 | Brooks |
| 2,832,245 A | 4/1958 | Burrows |
| 2,895,368 A | 7/1959 | Place |
| 3,462,765 A | 8/1969 | Swanson |
| 3,466,669 A | 9/1969 | Flatt |
| 3,593,342 A | 7/1971 | Niebauer et al. |
| 3,681,786 A | 8/1972 | Lynch |
| 3,739,403 A | 6/1973 | Nicolle |
| 3,759,257 A | 9/1973 | Fischer et al. |
| 3,760,802 A | 9/1973 | Fischer et al. |
| 3,779,239 A | 12/1973 | Fischer et al. |
| 3,824,631 A | 7/1974 | Burstein et al. |
| D243,716 S | 3/1977 | Treace et al. |
| 4,047,524 A | 9/1977 | Hall |
| 4,096,896 A | 6/1978 | Engel |
| 4,156,296 A | 5/1979 | Johnson et al. |
| 4,170,990 A | 10/1979 | Baumgart et al. |
| 4,175,555 A | 11/1979 | Herbert |
| 4,198,713 A | 4/1980 | Swanson |
| 4,204,284 A | 5/1980 | Koeneman |
| 4,213,208 A | 7/1980 | Marne |
| 4,237,875 A | 12/1980 | Termanini |
| 4,262,665 A | 4/1981 | Roalstad et al. |
| 4,263,903 A | 4/1981 | Griggs |
| 4,275,717 A | 6/1981 | Bolesky |
| 4,276,660 A | 7/1981 | Laure |
| 4,278,091 A | 7/1981 | Borzone |
| 4,304,011 A | 12/1981 | Whelan, III |
| 4,321,002 A | 3/1982 | Froehlich |
| 4,364,382 A | 12/1982 | Mennen |
| 4,367,562 A | 1/1983 | Gauthier |
| 4,404,874 A | 9/1983 | Lieser |
| 4,434,796 A | 3/1984 | Karapetian et al. |
| 4,454,875 A | 6/1984 | Pratt et al. |
| 4,485,816 A | 12/1984 | Krumme |
| D277,509 S | 2/1985 | Lawrence et al. |
| D277,784 S | 2/1985 | Sgariato et al. |
| 4,516,569 A | 5/1985 | Evans et al. |
| 4,570,623 A | 2/1986 | Ellison et al. |
| 4,590,928 A | 5/1986 | Hunt et al. |
| D284,099 S | 6/1986 | Laporta et al. |
| 4,634,382 A | 1/1987 | Kusano et al. |
| 4,642,122 A | 2/1987 | Stefee |
| 4,655,661 A | 4/1987 | Brandt |
| D291,731 S | 9/1987 | Alkins |
| 4,723,540 A | 2/1988 | Gilmer, Jr. |
| 4,723,541 A | 2/1988 | Reese |
| 4,731,087 A | 3/1988 | Sculco et al. |
| 4,756,711 A | 7/1988 | Mai et al. |
| 4,759,768 A | 7/1988 | Hermann et al. |
| 4,790,304 A | 12/1988 | Rosenberg |
| 4,865,606 A | 9/1989 | Rehder |
| 4,908,031 A | 3/1990 | Frisch |
| 4,915,092 A | 4/1990 | Firica et al. |
| 4,932,974 A | 6/1990 | Pappas et al. |
| 4,940,467 A | 7/1990 | Tronzo |
| 4,955,916 A | 9/1990 | Carignan et al. |
| 4,963,144 A | 10/1990 | Huene |
| 4,969,909 A | 11/1990 | Barouk |
| 5,002,563 A | 3/1991 | Pyka et al. |
| 5,007,932 A | 4/1991 | Bekki et al. |
| 5,011,497 A | 4/1991 | Persson et al. |
| 5,019,079 A | 5/1991 | Ross |
| 5,029,753 A | 7/1991 | Hipon et al. |
| 5,037,440 A | 8/1991 | Koenig |
| 5,046,513 A | 9/1991 | Gatturna et al. |
| 5,047,059 A | 9/1991 | Saffar |
| 5,053,038 A | 10/1991 | Sheehan |
| 5,059,193 A | 10/1991 | Kuslich |
| 5,062,851 A | 11/1991 | Branemark |
| 5,089,009 A | 2/1992 | Green |
| 5,092,896 A | 3/1992 | Meuli et al. |
| 5,108,395 A | 4/1992 | Laurain |
| 5,133,761 A | 7/1992 | Krouskop |
| 5,147,363 A | 9/1992 | Harle |
| 5,171,252 A | 12/1992 | Friedland |
| 5,179,915 A | 1/1993 | Cohen et al. |
| 5,190,546 A | 3/1993 | Jervis |
| 5,199,839 A | 4/1993 | DeHaitre |
| 5,207,712 A | 5/1993 | Cohen |
| 5,209,756 A | 5/1993 | Seedhom et al. |
| 5,213,347 A | 5/1993 | Rulon et al. |
| 5,222,975 A | 6/1993 | Crainich |
| 5,236,431 A * | 8/1993 | Gogolewski ....... A61B 17/0642 606/139 |
| 5,246,443 A | 9/1993 | Mai |
| 5,281,225 A | 1/1994 | Vicenzi |
| 5,304,204 A | 4/1994 | Bregen |
| 5,324,307 A | 6/1994 | Jarrett et al. |
| 5,326,364 A | 7/1994 | Clift, Jr. et al. |
| 5,326,366 A | 7/1994 | Pascarella et al. |
| 5,330,476 A | 7/1994 | Hiot et al. |
| 5,342,396 A | 8/1994 | Cook |
| 5,352,229 A | 10/1994 | Goble et al. |
| 5,354,301 A | 10/1994 | Catellano |
| 5,358,405 A | 10/1994 | Imai |
| 5,360,450 A | 11/1994 | Giannini |
| 5,366,479 A | 11/1994 | McGarry et al. |
| 5,380,334 A | 1/1995 | Torrie et al. |
| 5,395,372 A | 3/1995 | Holt et al. |
| 5,405,400 A | 4/1995 | Linscheid et al. |
| 5,405,401 A | 4/1995 | Lippincott, III et al. |
| 5,417,692 A | 5/1995 | Goble et al. |
| 5,425,776 A | 6/1995 | Cohen |
| 5,425,777 A | 6/1995 | Sarkisian et al. |
| 5,437,674 A | 8/1995 | Worcel et al. |
| 5,449,359 A | 9/1995 | Groiso |
| 5,454,814 A | 10/1995 | Comte |
| 5,458,648 A | 10/1995 | Berman et al. |
| 5,470,230 A | 11/1995 | Daftary et al. |
| 5,474,557 A | 12/1995 | Mai |
| 5,480,447 A | 1/1996 | Skiba |
| 5,484,443 A | 1/1996 | Pascarella et al. |
| 5,498,265 A | 3/1996 | Asnis et al. |
| 5,507,822 A | 4/1996 | Bouchon et al. |
| 5,516,248 A | 5/1996 | DeHaitre |
| 5,522,903 A | 6/1996 | Sokolow et al. |
| 5,529,075 A | 6/1996 | Clark |
| 5,536,127 A | 7/1996 | Pennig |
| 5,549,681 A | 8/1996 | Segmüller et al. |
| 5,551,871 A | 9/1996 | Besselink et al. |
| 5,554,157 A | 9/1996 | Errico et al. |
| 5,578,034 A | 11/1996 | Estes |
| 5,591,165 A | 1/1997 | Jackson |
| 5,595,563 A | 1/1997 | Moisdon |
| 5,601,558 A | 2/1997 | Torrie et al. |
| D378,409 S | 3/1997 | Michelson |
| 5,634,925 A | 6/1997 | Urbanski |
| 5,643,264 A | 7/1997 | Sherman et al. |
| 5,645,599 A | 7/1997 | Samani |
| 5,660,188 A | 8/1997 | Groiso |
| 5,669,913 A | 9/1997 | Zobel |
| 5,674,297 A | 10/1997 | Lane et al. |
| 5,683,466 A | 11/1997 | Vitale |
| 5,690,629 A | 11/1997 | Asher et al. |
| 5,702,472 A | 12/1997 | Huebner |
| 5,707,395 A | 1/1998 | Li |
| 5,713,903 A | 2/1998 | Sander et al. |
| 5,713,904 A | 2/1998 | Errico et al. |
| 5,720,753 A | 2/1998 | Sander et al. |

(56) References Cited

U.S. PATENT DOCUMENTS

| | | | |
|---|---|---|---|
| 5,720,766 | A * | 2/1998 | Zang .......... A61B 17/0401 606/104 |
| 5,725,585 | A | 3/1998 | Zobel |
| 5,728,127 | A | 3/1998 | Asher et al. |
| 5,733,307 | A | 3/1998 | Dinsdale |
| 5,741,256 | A | 4/1998 | Bresina |
| 5,749,916 | A | 5/1998 | Richelsoph |
| 5,769,852 | A | 6/1998 | Brangnemark |
| 5,776,202 | A | 7/1998 | Copf et al. |
| 5,779,707 | A | 7/1998 | Bertholet et al. |
| 5,782,927 | A | 7/1998 | Klawittler et al. |
| 5,785,713 | A | 7/1998 | Jobe |
| 5,840,078 | A | 11/1998 | Yerys |
| 5,853,414 | A | 12/1998 | Groiso |
| 5,876,434 | A | 3/1999 | Flomenblit et al. |
| 5,882,444 | A | 3/1999 | Flomenblit et al. |
| 5,893,850 | A | 4/1999 | Cachia |
| 5,919,193 | A | 7/1999 | Slavitt |
| 5,928,236 | A | 7/1999 | Augagneur et al. |
| 5,941,890 | A | 8/1999 | Voegele et al. |
| 5,951,288 | A | 9/1999 | Sawa |
| 5,958,159 | A | 9/1999 | Prandi |
| 5,980,524 | A | 11/1999 | Justin et al. |
| 5,984,970 | A | 11/1999 | Bramlet |
| 5,984,971 | A | 11/1999 | Faccioli et al. |
| 6,011,497 | A | 1/2000 | Tsang et al. |
| 6,017,366 | A | 1/2000 | Berman |
| 6,030,162 | A | 2/2000 | Huebner |
| 6,045,573 | A | 4/2000 | Wenstrom, Jr. et al. |
| 6,048,151 | A | 4/2000 | Kwee |
| 6,048,343 | A | 4/2000 | Mathis et al. |
| 6,083,242 | A | 7/2000 | Cook |
| 6,099,571 | A | 8/2000 | Knapp |
| 6,102,642 | A | 8/2000 | Kawashita et al. |
| 6,146,387 | A | 11/2000 | Trott et al. |
| 6,187,009 | B1 | 2/2001 | Herzog et al. |
| 6,193,757 | B1 | 2/2001 | Foley et al. |
| 6,197,037 | B1 | 3/2001 | Hair |
| 6,200,321 | B1 | 3/2001 | Orbay et al. |
| 6,200,330 | B1 | 3/2001 | Benderev et al. |
| 6,200,345 | B1 | 3/2001 | Morgan |
| 6,224,600 | B1 | 5/2001 | Protogirou |
| 6,248,109 | B1 | 6/2001 | Stofella |
| 6,299,613 | B1 | 10/2001 | Ogilvie et al. |
| 6,305,053 | B1 | 10/2001 | Galbreath |
| 6,306,140 | B1 | 10/2001 | Siddiqui |
| 6,319,284 | B1 | 11/2001 | Rushdy et al. |
| 6,332,885 | B1 | 12/2001 | Martella |
| 6,336,928 | B1 | 1/2002 | Guerin et al. |
| 6,352,560 | B1 | 3/2002 | Poeschmann et al. |
| 6,383,223 | B1 | 5/2002 | Baehler et al. |
| 6,386,877 | B1 | 5/2002 | Sutter |
| 6,406,234 | B2 | 6/2002 | Frigg |
| 6,413,260 | B1 | 7/2002 | Berrevoets et al. |
| 6,419,706 | B1 | 7/2002 | Graf |
| 6,423,097 | B2 | 7/2002 | Rauscher |
| 6,428,634 | B1 | 8/2002 | Besselink et al. |
| 6,436,099 | B1 | 8/2002 | Drewry et al. |
| 6,451,057 | B1 | 9/2002 | Chen et al. |
| 6,454,808 | B1 | 9/2002 | Masada |
| 6,458,134 | B1 | 10/2002 | Songer et al. |
| 6,475,242 | B1 | 11/2002 | Bramlet |
| 6,508,841 | B2 | 1/2003 | Martin et al. |
| 6,517,543 | B1 | 2/2003 | Berrevoets et al. |
| 6,533,788 | B1 | 3/2003 | Orbay |
| 6,551,321 | B1 | 4/2003 | Burkinshaw |
| 6,551,343 | B1 | 4/2003 | Törmälä et al. |
| 6,575,973 | B1 | 6/2003 | Shekalim |
| 6,575,976 | B2 | 6/2003 | Grafton |
| 6,582,453 | B1 | 6/2003 | Tran et al. |
| 6,648,890 | B2 | 11/2003 | Culbert et al. |
| 6,679,668 | B2 | 1/2004 | Martin et al. |
| 6,682,565 | B1 | 1/2004 | Krishnan |
| 6,685,706 | B2 | 2/2004 | Padget et al. |
| 6,699,247 | B2 | 3/2004 | Zucherman et al. |
| 6,699,292 | B2 | 3/2004 | Ogilvie et al. |
| 6,706,045 | B2 | 3/2004 | Lin et al. |
| 6,767,350 | B1 | 7/2004 | Lob |
| 6,773,437 | B2 | 8/2004 | Ogilvie et al. |
| 6,811,568 | B2 | 11/2004 | Minamikawa |
| 6,869,449 | B2 | 3/2005 | Ball et al. |
| 6,875,235 | B2 | 4/2005 | Ferree |
| 7,037,309 | B2 | 5/2006 | Weil et al. |
| 7,037,324 | B2 | 5/2006 | Martinek |
| 7,037,342 | B2 | 5/2006 | Nilsson et al. |
| 7,041,106 | B1 | 5/2006 | Carver et al. |
| 7,044,953 | B2 | 5/2006 | Capanni |
| 7,112,214 | B2 | 9/2006 | Peterson et al. |
| 7,182,787 | B2 | 2/2007 | Hassler et al. |
| 7,192,445 | B2 | 3/2007 | Ellingsen et al. |
| 7,207,994 | B2 | 4/2007 | Vlahos et al. |
| 7,240,677 | B2 | 7/2007 | Fox |
| 7,261,716 | B2 | 8/2007 | Strobel |
| 7,291,175 | B1 | 11/2007 | Gordon |
| 7,569,061 | B2 | 8/2009 | Colleran |
| 7,585,316 | B2 | 9/2009 | Trieu |
| 7,588,603 | B2 | 9/2009 | Leonard |
| 7,695,471 | B2 | 4/2010 | Cheung et al. |
| 7,708,759 | B2 | 5/2010 | Lubbers et al. |
| 7,727,235 | B2 | 6/2010 | Contiliano et al. |
| 7,780,701 | B1 | 8/2010 | Meridew et al. |
| 7,780,737 | B2 | 8/2010 | Bonnard et al. |
| 7,785,357 | B2 | 8/2010 | Guan et al. |
| 7,824,091 | B2 | 11/2010 | Johnstone et al. |
| 7,837,738 | B2 | 11/2010 | Reigstad et al. |
| 7,887,589 | B2 | 2/2011 | Glenn et al. |
| 7,909,880 | B1 | 3/2011 | Grant |
| 7,918,879 | B2 | 4/2011 | Yeung et al. |
| 7,959,681 | B2 | 6/2011 | Lavi |
| 7,963,995 | B2 | 6/2011 | Richelsoph |
| 7,976,565 | B1 | 7/2011 | Meridew |
| 7,985,246 | B2 | 7/2011 | Trieu |
| 8,002,811 | B2 | 8/2011 | Corradi et al. |
| 8,057,524 | B2 | 11/2011 | Meridew |
| 8,100,983 | B2 | 1/2012 | Schulte |
| 8,118,839 | B2 | 2/2012 | Taylor |
| 8,118,849 | B2 | 2/2012 | Wahl et al. |
| 8,197,509 | B2 | 6/2012 | Contiliano et al. |
| 8,262,712 | B2 | 9/2012 | Coilard-Lavirotte et al. |
| 8,267,939 | B2 | 9/2012 | Cipoletti et al. |
| 8,337,537 | B2 | 12/2012 | Pelo et al. |
| 8,394,097 | B2 | 3/2013 | Peyrot et al. |
| 8,394,132 | B2 | 3/2013 | Lewis et al. |
| 8,414,583 | B2 | 4/2013 | Prandi et al. |
| 8,465,525 | B2 | 6/2013 | Hawkins et al. |
| 8,475,456 | B2 | 7/2013 | Augoyard et al. |
| 8,523,944 | B2 | 9/2013 | Jiminez et al. |
| 8,591,545 | B2 | 11/2013 | Lunn et al. |
| 8,608,785 | B2 | 12/2013 | Reed et al. |
| 8,616,091 | B2 | 12/2013 | Anderson |
| 8,636,457 | B2 | 1/2014 | Connors |
| 8,641,769 | B2 | 2/2014 | Malandain |
| 8,647,390 | B2 | 2/2014 | Bellemere et al. |
| 8,764,842 | B2 | 7/2014 | Graham |
| 8,840,677 | B2 | 9/2014 | Kale et al. |
| 8,888,779 | B2 | 11/2014 | Senn |
| D720,072 | S | 12/2014 | Cheney et al. |
| 8,906,060 | B2 | 12/2014 | Hart |
| 8,986,386 | B2 | 3/2015 | Oglaza et al. |
| 8,998,999 | B2 | 4/2015 | Lewis et al. |
| 9,044,287 | B2 | 6/2015 | Reed et al. |
| 9,056,014 | B2 | 6/2015 | McCormick et al. |
| 9,125,704 | B2 | 9/2015 | Reed et al. |
| 9,138,274 | B1 | 9/2015 | Biesinger et al. |
| 9,149,268 | B2 | 10/2015 | Graul et al. |
| 2001/0025199 | A1 | 9/2001 | Rauscher |
| 2001/0028836 | A1 | 10/2001 | Kohori |
| 2001/0049529 | A1 | 12/2001 | Cachia et al. |
| 2002/0019636 | A1 | 2/2002 | Ogilvie et al. |
| 2002/0022887 | A1 | 2/2002 | Huene |
| 2002/0026194 | A1 | 2/2002 | Morrison et al. |
| 2002/0055785 | A1 | 5/2002 | Harris |
| 2002/0065561 | A1 | 5/2002 | Ogilvie et al. |
| 2002/0068939 | A1 | 6/2002 | Levy et al. |

(56) References Cited

U.S. PATENT DOCUMENTS

| | | |
|---|---|---|
| 2002/0072803 A1 | 6/2002 | Saunders et al. |
| 2002/0082705 A1 | 6/2002 | Bouman et al. |
| 2002/0111690 A1 | 8/2002 | Hyde |
| 2002/0128713 A1 | 9/2002 | Ferree |
| 2002/0165544 A1 | 11/2002 | Perren et al. |
| 2002/0183846 A1 | 12/2002 | Kuslich et al. |
| 2003/0032961 A1 | 2/2003 | Pelo et al. |
| 2003/0040805 A1 | 2/2003 | Minamikawa |
| 2003/0069645 A1 | 4/2003 | Ball et al. |
| 2003/0074004 A1* | 4/2003 | Reed ............... A61B 17/8057 606/311 |
| 2003/0130660 A1 | 7/2003 | Levy et al. |
| 2003/0191422 A1 | 10/2003 | Sossong |
| 2003/0233095 A1 | 12/2003 | Urbanski et al. |
| 2004/0010315 A1 | 1/2004 | Song |
| 2004/0093081 A1 | 5/2004 | Nilsson et al. |
| 2004/0097941 A1 | 5/2004 | Weiner et al. |
| 2004/0102853 A1 | 5/2004 | Boumann et al. |
| 2004/0111117 A1 | 6/2004 | Colleran et al. |
| 2004/0133204 A1 | 7/2004 | Davies |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2004/0230194 A1 | 11/2004 | Urbanski et al. |
| 2004/0230313 A1 | 11/2004 | Saunders |
| 2004/0249461 A1 | 12/2004 | Ferree |
| 2005/0038438 A1* | 2/2005 | Anderson .......... A61B 17/7071 606/304 |
| 2005/0113836 A1 | 5/2005 | Lozier et al. |
| 2005/0119757 A1 | 6/2005 | Hassler et al. |
| 2005/0123672 A1 | 6/2005 | Justin et al. |
| 2005/0124443 A1 | 6/2005 | Summers |
| 2005/0149031 A1 | 7/2005 | Ciccone et al. |
| 2005/0177158 A1 | 8/2005 | Doubler et al. |
| 2005/0187636 A1 | 8/2005 | Graham |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0052725 A1 | 3/2006 | Santilli |
| 2006/0052878 A1 | 3/2006 | Schmieding |
| 2006/0074421 A1 | 4/2006 | Bickley et al. |
| 2006/0074488 A1 | 4/2006 | Abdou |
| 2006/0074492 A1 | 4/2006 | Frey |
| 2006/0084998 A1 | 4/2006 | Levy et al. |
| 2006/0100715 A1 | 5/2006 | De Villiers |
| 2006/0129153 A1 | 6/2006 | Klaue et al. |
| 2006/0149258 A1 | 6/2006 | Sousa |
| 2006/0173462 A1 | 8/2006 | Kay et al. |
| 2006/0200151 A1 | 9/2006 | Ducharme et al. |
| 2006/0229617 A1 | 10/2006 | Meller et al. |
| 2006/0247787 A1 | 11/2006 | Rydell et al. |
| 2007/0038303 A1 | 2/2007 | Myerson et al. |
| 2007/0078518 A1 | 4/2007 | Lavi |
| 2007/0106283 A1 | 5/2007 | Garcia et al. |
| 2007/0123873 A1 | 5/2007 | Czartoski et al. |
| 2007/0123993 A1 | 5/2007 | Hassler et al. |
| 2007/0142920 A1 | 6/2007 | Niemi |
| 2007/0177959 A1 | 8/2007 | Chopp et al. |
| 2007/0185583 A1 | 8/2007 | Branemark |
| 2007/0185584 A1 | 8/2007 | Kaufmann et al. |
| 2007/0198018 A1 | 8/2007 | Biedermann et al. |
| 2007/0213831 A1 | 9/2007 | de Cubber |
| 2007/0239158 A1 | 10/2007 | Trieu et al. |
| 2007/0293866 A1 | 12/2007 | Stroeckel et al. |
| 2008/0039949 A1 | 2/2008 | Meesenburg et al. |
| 2008/0051912 A1 | 2/2008 | Hollawell |
| 2008/0086139 A1 | 4/2008 | Bourke et al. |
| 2008/0132894 A1 | 6/2008 | Coilard-Lavirotte et al. |
| 2008/0132958 A1 | 6/2008 | Pech et al. |
| 2008/0154385 A1 | 6/2008 | Trail et al. |
| 2008/0161919 A1 | 7/2008 | Melkent |
| 2008/0177262 A1 | 7/2008 | Augoyard et al. |
| 2008/0177291 A1 | 7/2008 | Jensen et al. |
| 2008/0177334 A1 | 7/2008 | Stinnette |
| 2008/0195215 A1 | 8/2008 | Morton |
| 2008/0195219 A1 | 8/2008 | Wiley et al. |
| 2008/0221574 A1 | 9/2008 | Cavallazzi |
| 2008/0221697 A1 | 9/2008 | Graser |
| 2008/0221698 A1 | 9/2008 | Berger |
| 2008/0255618 A1 | 10/2008 | Fisher et al. |
| 2008/0269908 A1 | 10/2008 | Warburton |
| 2008/0294204 A1 | 11/2008 | Chirico et al. |
| 2009/0005782 A1 | 1/2009 | Chirico et al. |
| 2009/0012564 A1 | 1/2009 | Chirico et al. |
| 2009/0036893 A1 | 2/2009 | Kerteilan et al. |
| 2009/0105767 A1 | 4/2009 | Reiley |
| 2009/0163918 A1 | 6/2009 | Levy et al. |
| 2009/0187219 A1 | 7/2009 | Pachtman et al. |
| 2009/0204158 A1 | 8/2009 | Sweeney |
| 2009/0210016 A1 | 8/2009 | Champagne et al. |
| 2009/0216282 A1 | 8/2009 | Blake et al. |
| 2009/0254189 A1 | 10/2009 | Scheker |
| 2009/0254190 A1 | 10/2009 | Gannoe et al. |
| 2009/0259316 A1 | 10/2009 | Ginn et al. |
| 2009/0149891 A1 | 11/2009 | Lee et al. |
| 2010/0010637 A1 | 1/2010 | Pequignot |
| 2010/0016982 A1 | 1/2010 | Solomons |
| 2010/0023012 A1 | 1/2010 | Voor |
| 2010/0030221 A1 | 2/2010 | Christian et al. |
| 2010/0049244 A1 | 2/2010 | Cohen et al. |
| 2010/0057214 A1 | 3/2010 | Graham et al. |
| 2010/0061825 A1 | 3/2010 | Liu et al. |
| 2010/0069970 A1 | 3/2010 | Lewis et al. |
| 2010/0121390 A1 | 5/2010 | Kleinman |
| 2010/0125274 A1 | 5/2010 | Greenhalgh et al. |
| 2010/0131014 A1 | 5/2010 | Peyrot et al. |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0217325 A1 | 8/2010 | Hochschuler et al. |
| 2010/0249942 A1 | 9/2010 | Goswami et al. |
| 2010/0256639 A1 | 10/2010 | Tyber et al. |
| 2010/0256770 A1 | 10/2010 | Hakansson et al. |
| 2010/0262254 A1 | 10/2010 | Lawrence et al. |
| 2010/0274293 A1 | 10/2010 | Terrill et al. |
| 2010/0286692 A1 | 11/2010 | Greenhalgh et al. |
| 2010/0292799 A1 | 11/2010 | Hansell et al. |
| 2010/0324556 A1 | 12/2010 | Tyber et al. |
| 2010/0331893 A1 | 12/2010 | Geist et al. |
| 2011/0004255 A1 | 1/2011 | Weiner et al. |
| 2011/0004317 A1 | 1/2011 | Hacking et al. |
| 2011/0066190 A1 | 3/2011 | Schaller et al. |
| 2011/0082507 A1 | 4/2011 | Klaue |
| 2011/0082508 A1 | 4/2011 | Reed |
| 2011/0093017 A1 | 4/2011 | Prasad et al. |
| 2011/0093075 A1 | 4/2011 | Duplessis et al. |
| 2011/0093085 A1 | 4/2011 | Morton |
| 2011/0118739 A1 | 5/2011 | Tyber et al. |
| 2011/0144644 A1 | 6/2011 | Prandi et al. |
| 2011/0144766 A1 | 6/2011 | Kale et al. |
| 2011/0208252 A1 | 8/2011 | Erhart |
| 2011/0257652 A1 | 10/2011 | Roman |
| 2011/0301652 A1 | 12/2011 | Reed et al. |
| 2011/0301653 A1 | 12/2011 | Reed et al. |
| 2011/0306975 A1 | 12/2011 | Kaikkonen et al. |
| 2011/0319946 A1 | 12/2011 | Levy et al. |
| 2012/0016428 A1 | 1/2012 | White et al. |
| 2012/0065692 A1 | 3/2012 | Champagne et al. |
| 2012/0065738 A1 | 3/2012 | Schulman |
| 2012/0089197 A1 | 4/2012 | Anderson |
| 2012/0136448 A1 | 5/2012 | Seifert et al. |
| 2012/0209337 A1 | 8/2012 | Weinstein |
| 2012/0259419 A1 | 10/2012 | Brown et al. |
| 2012/0271362 A1 | 10/2012 | Martineau et al. |
| 2012/0323241 A1 | 12/2012 | McClellan et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1 | 3/2013 | Anderson et al. |
| 2013/0066435 A1 | 3/2013 | Averous et al. |
| 2013/0079776 A1 | 3/2013 | Zwirkoski et al. |
| 2013/0090655 A1 | 4/2013 | Tontz |
| 2013/0096634 A1 | 4/2013 | Suh |

(56) References Cited

U.S. PATENT DOCUMENTS

| | | | |
|---|---|---|---|
| 2013/0123862 A1 | 5/2013 | Anderson et al. |
| 2013/0131822 A1 | 5/2013 | Lewis et al. |
| 2013/0150965 A1 | 6/2013 | Taylor et al. |
| 2013/0190761 A1 | 7/2013 | Prandi et al. |
| 2013/0211451 A1 | 8/2013 | Wales et al. |
| 2013/0226191 A1 | 8/2013 | Thoren et al. |
| 2013/0253597 A1 | 9/2013 | Augoyard et al. |
| 2013/0274814 A1 | 10/2013 | Weiner et al. |
| 2013/0317559 A1 | 11/2013 | Leavitt et al. |
| 2013/0325138 A1 | 12/2013 | Graham |
| 2014/0018930 A1 | 1/2014 | Oster |
| 2014/0025125 A1 | 1/2014 | Sack et al. |
| 2014/0052196 A1 | 2/2014 | McGinley et al. |
| 2014/0107713 A1 | 4/2014 | Pech et al. |
| 2014/0135768 A1 | 5/2014 | Roman |
| 2014/0142715 A1 | 5/2014 | McCormick |
| 2014/0180428 A1 | 6/2014 | McCormick |
| 2014/0188179 A1 | 7/2014 | McCormick |
| 2014/0188237 A1 | 7/2014 | McCormick et al. |
| 2014/0188239 A1 | 7/2014 | Cummings |
| 2014/0257289 A1 | 9/2014 | Kecman et al. |
| 2014/0276825 A1 | 9/2014 | Brown et al. |
| 2014/0277185 A1 | 9/2014 | Boileau et al. |
| 2014/0277186 A1 | 9/2014 | Granberry et al. |
| 2014/0277191 A1* | 9/2014 | Evans ............... A61B 17/7225 606/308 |
| 2014/0277554 A1* | 9/2014 | Roman ............... A61F 2/4225 623/21.19 |
| 2015/0011998 A1* | 1/2015 | McCormick ........... A61F 5/019 606/56 |
| 2015/0012098 A1 | 1/2015 | Eastlack et al. |
| 2015/0018954 A1 | 1/2015 | Loebl et al. |
| 2015/0073413 A1 | 3/2015 | Palmer et al. |
| 2015/0088136 A1 | 3/2015 | Vitek et al. |
| 2015/0088266 A1 | 3/2015 | Sander et al. |
| 2015/0094778 A1 | 4/2015 | McCormick et al. |
| 2015/0112342 A1 | 4/2015 | Penzimer et al. |
| 2015/0141994 A1 | 5/2015 | Cheney et al. |
| 2015/0142066 A1 | 5/2015 | Shemwell et al. |
| 2015/0164563 A1 | 6/2015 | Lewis et al. |
| 2015/0223848 A1 | 8/2015 | McCormick et al. |
| 2015/0223849 A1 | 8/2015 | McCormick et al. |
| 2015/0342655 A1 | 12/2015 | Reed et al. |
| 2016/0081728 A1 | 3/2016 | McCormick |

FOREIGN PATENT DOCUMENTS

| | | |
|---|---|---|
| EP | 0127994 | 12/1984 |
| EP | 0340159 A1 | 11/1989 |
| EP | 0409364 A2 | 1/1991 |
| EP | 0545830 | 6/1993 |
| EP | 0551846 A1 | 7/1993 |
| EP | 0611557 A3 | 8/1994 |
| EP | 0738502 A2 | 10/1996 |
| EP | 880950 A1 | 12/1998 |
| EP | 1300122 | 4/2003 |
| EP | 1825826 A1 | 8/2007 |
| EP | 1 870 050 A2 | 12/2007 |
| EP | 1708653 B1 | 9/2009 |
| EP | 1923012 B1 | 6/2010 |
| EP | 1868536 B1 | 11/2010 |
| EP | 2275055 B1 | 5/2012 |
| EP | 2221025 B1 | 12/2012 |
| EP | 2221026 B1 | 3/2013 |
| EP | 2564799 A1 | 3/2013 |
| EP | 2774556 A1 | 9/2014 |
| FR | 736058 | 11/1932 |
| FR | 1036978 | 9/1953 |
| FR | 2603794 | 3/1988 |
| FR | 2605878 A1 | 5/1988 |
| FR | 2628312 | 9/1989 |
| FR | 2645735 A1 | 10/1990 |
| FR | 2651119 A1 | 3/1991 |
| FR | 2663838 A1 | 1/1993 |
| FR | 2694696 | 2/1994 |
| FR | 2725126 | 4/1996 |
| FR | 2743490 | 7/1997 |
| FR | 2754702 | 4/1998 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A1 | 5/2004 |
| FR | 2728779 A1 | 7/2005 |
| FR | 2884406 | 10/2006 |
| FR | 2927529 A1 | 8/2009 |
| FR | 2935601 A1 | 3/2010 |
| GB | 140983 | 4/1920 |
| GB | 2119655 A | 11/1983 |
| GB | 2227540 A | 8/1990 |
| GB | 2336415 A | 10/1999 |
| GB | 2430625 A | 4/2007 |
| JP | S53-128181 A | 11/1978 |
| JP | 60145133 | 7/1985 |
| JP | H07-500520 A | 1/1995 |
| JP | 07303662 | 11/1995 |
| JP | 2004535249 | 11/2004 |
| JP | 2007530194 | 11/2007 |
| JP | 2008-188411 A | 8/2008 |
| JP | 2009-160399 A | 7/2009 |
| JP | 2010-046481 A | 3/2010 |
| JP | 2011-502584 A | 1/2011 |
| JP | 2011-525229 A | 9/2011 |
| SU | 1152582 | 4/1985 |
| WO | WO 92/17122 | 10/1992 |
| WO | WO 96/41596 A1 | 12/1996 |
| WO | WO 98/17189 | 4/1998 |
| WO | WO 98/47449 A1 | 10/1998 |
| WO | WO 99/21515 A1 | 5/1999 |
| WO | WO 01/80751 A1 | 11/2001 |
| WO | WO 2002/034107 A2 | 5/2002 |
| WO | WO 2005/063149 | 7/2005 |
| WO | WO 2005/094706 A1 | 10/2005 |
| WO | WO 2005/104961 | 11/2005 |
| WO | WO 2006/109004 A1 | 10/2006 |
| WO | WO 2006103598 A1 | 10/2006 |
| WO | WO 2007/048038 | 4/2007 |
| WO | WO 2007/135322 A1 | 11/2007 |
| WO | WO 2009/155577 A2 | 12/2009 |
| WO | WO 2013/096746 A1 | 6/2013 |
| WO | WO 2013/131974 A1 | 9/2013 |
| WO | 2014165123 A1 | 10/2014 |

OTHER PUBLICATIONS

Brochure p/n 030-1788 Rev A: ExtremiFuse Hammertoe Fixation System, OsteoMED Smalll Bone Orthopedics, 6 pages, undated.

Brochure 900-01-008 Rev C: Hammer Toe Implant System Instructions for Use, Trilliant Surgical Ltd, 2 pages, undated.

Bensmann, et al., "Nickel-titanium Osteosynthesis Clips," Reprint from Medical Focus, 1983.

Besselink, Sachdeva, "Applications of Shape Memory Effects," Memory Metal Holland, Memory Medical Systems, Publication Date Unknown.

Dai, K.R., et al., "Treatment of Intra-Articular Fractures with Shape Memory Compression Staples," Injury, (1993) 24, (IO), 651-655.

Haasters, Dr. J., et al. , "The Use of Ni—Ti As an Implant Material in Orthopedics", pp. 426-444.

Kuo, M.D., et al., "The Use of Nickel-Titanium Alloy in Orthopedic Surgery in China," Orthopedics, Jan. 1989, vol. 12/No. 1.

Lu, M.D., Shibi,"Medical Applications of Ni—Ti Alloys in China," pp. 445-451.

Ricart, "The Use of a Memory Shape Staple in Cervical Anterior Fusion," Proceedings of the Second International Conference on Shape Memory and Superelastic Technologies, Asilomar Conference Center, Pacific Grove, CA, USA, Mar. 2-6, 1997.

Ricart, "The Use of a Memory-Shaple Staple in Cervical Anterior Fusion," in Shape Memory Implants, Springer-Verlag Berlin Heidelberg, 2000.

Tang, Dai, Chen ,"Application of a Ni—Ti Staple in the Metatarsal Osteotomy," Bio-Medical Materials and Engineering 6, (1996), 307-312, IOS Press.

(56) References Cited

OTHER PUBLICATIONS

International Application Division, Korean Intellectual Property Office, The International Searching Authority, PCT International International Search Report and Written Opinion regarding corresponding PCT Application No. PCT/US2014/071526 dated Sep. 1, 2015, pp. 1-13.
Examination Report No. 3 issued for corresponding Australian patent application No. 2014334525, dated Apr. 13, 2017, 4 pages.

* cited by examiner

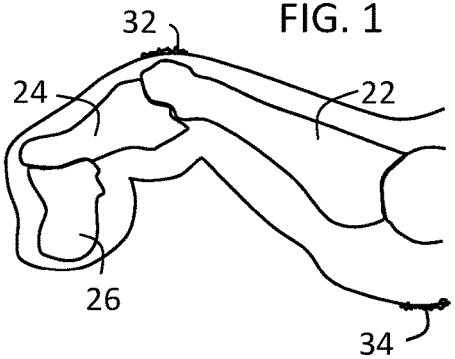
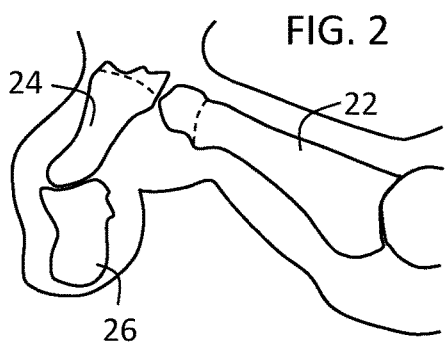
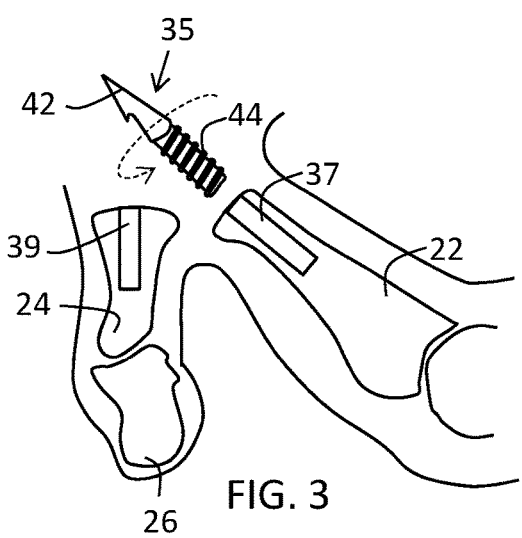
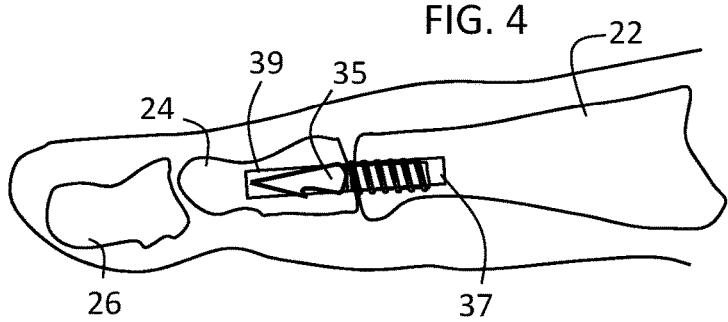

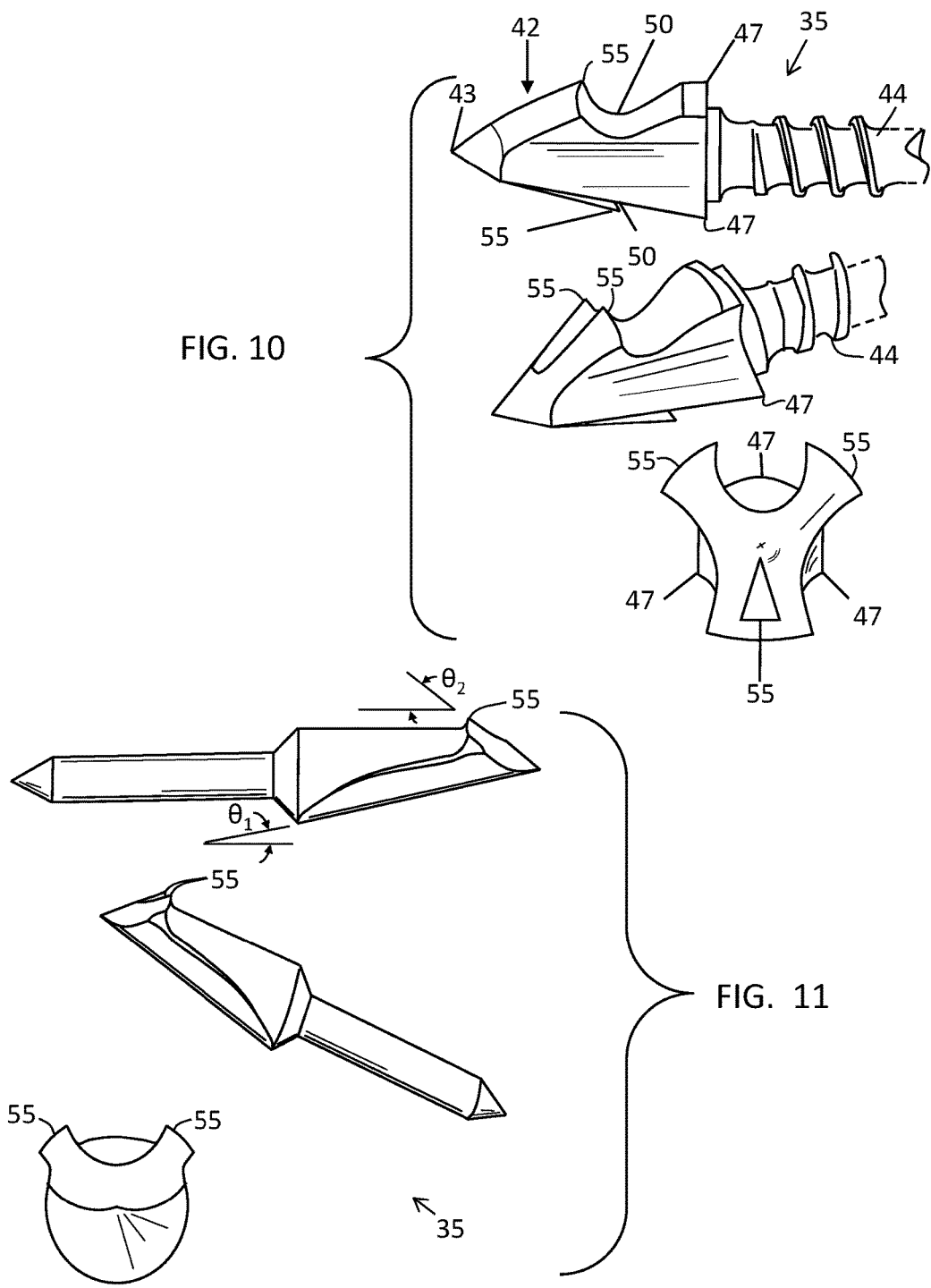

INTRAMEDULLARY ANCHOR FOR INTERPHALANGEAL ARTHRODESIS

CROSS REFERENCE TO RELATED APPLICATIONS

This application is a national phase entry under 35 U.S.C. 371 of international patent application No. PCT/US14/71526, filed Dec. 19, 2014, the entirety of which is incorporated herein by reference.

BACKGROUND

This disclosure relates to the field of surgical repair of phalangeal deformities such as hammer toe, by arthrodesis. An intramedullary anchor structure has an asymmetrically tapered barbed point enabling the point to be inserted over a range of starting angles relative to a longitudinal bore in a phalanx during a surgical procedure. The asymmetric point is configured to align the anchor structure to the bore when fully inserted, and fix the anchor structure against retraction from the bore.

A hammer toe or contracted toe is a deformity of the proximal interphalangeal joint of the second, third, or fourth toe, typically arising if the proximal phalanx at the proximal interphalangeal joint is habitually oriented upward while the more distal phalanges are curved over and downward, for example due to tight or poorly fit shoes. The muscles and joints of the toe assume a permanent contracted hammer shape. Wear points can develop calluses or corns, especially on the superior side of the proximal joint.

A hammer toe condition can be corrected by podiatric surgery. Traditional hammer toe arthrodesis (fusing) has the object of resetting and fusing the anatomical alignment of the phalanges at the proximal interphalangeal joint. A percutaneous intramedullary support known as a Kirschner-wire or K-wire, comprising a length of stiff metal wire, is embedded by insertion lengthwise through the distal phalanx, and lengthwise through the distal and proximal interphalangeal joints. A protruding end of the K-wire remains accessible at the distal end of the toe. The K-wire immobilizes the phalanges in a more nearly co-linear horizontal configuration. After a period of healing sufficient for the bones to fuse across the proximal interphalangeal joint, for example six weeks, the K-wire is removed, i.e., retracted lengthwise from the distal end of the toe.

K-wire arthodesis has some drawbacks including the need for the K-wire to traverse and potentially interfere unnecessarily with the distal interphalangeal joint. There are potential issues with infection due to the protruding wire. An alternative arthrodesis technique is to incise and dislocate the toe at the proximal interphalangeal joint and to insert and permanently embed an intramedullary support into both of the phalanges at the proximal interphalangeal joint, without insertion from the end of the toe. The intramedullary support, such as a short length of K-wire or another elongated supporting structure, is inserted into longitudinal bores extending proximally into the third phalanx and distally into the second phalanx. That is, the support is inserted oppositely endwise into both of the two phalanges that abut at the proximal phalangeal joint.

It is desirable for the elongated intramedullary support to extend well into both phalanges for good structural support. The intramedullary support should bottom out substantially in the bores formed in both phalanges when the phalanges are in abutment, to reduce the opportunity for displacement of the bones away from abutment where the bones are to be fused. After forming the bores, it is necessary to insert the intramedullary support endwise into the bore of the one of the two phalanges, and then relatively to displace the phalanges longitudinally away from one another by a sufficient distance to clear the protruding length of the intramedullary support.

For example, an intramedullary support might be inserted first in the proximal phalanx of the proximal interphalangeal joint, proximally up to the point of bottoming out in the bore. The length of the intramedullary support that protrudes from the proximal phalanx is equal to the length of the bore in the next distal phalanx so the support will bottom out there as well. The protruding length could be, for example, 75% of the length of the next distal phalanx, namely the length of the bore therein. In order to complete the assembly, the phalanges are pulled longitudinally apart, by at least the protruding length of the intramedullary support. While holding the phalanges in co-linear alignment, the bore in the distal phalanx is aligned with the protruding end of the intramedullary support, and the distal phalanx then is pushed proximally along the intramedullary support to abut against the proximal phalanx.

A short length of K-wire can be used as a permanent intramedullary support, bridging across the proximal interphalangeal joint but not protruding distally from the end of the toe. There are also intramedullary hammer toe implants with other structures available. One object of the intramedullary support is to immobilize the phalanges in abutment at the joint, namely to prevent relative displacement of the phalanges, which would delay or prevent them from fusing. One-way intramedullary structures are possible, for example, with barbed ends. An oppositely barbed intramedullary support is disclosed, for example, in US 2011/0257652-Roman. Embodiments with one end threaded and the other end barbed are disclosed in US 2013/0131822-Lewis. These disclosures are incorporated herein by reference. At least one barbed end is advantageous because when the bones at the joint are pushed onto a barbed intramedullary, the points or flukes of the barbed ends engage in the bone tissue, preventing retraction, and to some extent, preventing relative rotation of the bones. However regardless of engaging structure, in order to insert the intramedullary into the second of the two bones at the joint, the bones need to be separated longitudinally by the protruding length of the intramedullary, namely the length that is to be inserted into the second of the two bones.

The object is to re-position the phalanges substantially co-linearly at the joint, both phalanges being horizontal along their longitudinal extensions or having a slight plantar flex, e.g., 10°, and to fuse the phalanges across the joint in that orientation. The surgical procedure includes an incision on the superior side of the joint. The joint is dislocated for access through the incision to the abutting ends of the phalanges. The ends of one or both of the phalanges can be resected. For example, the distal phalange can be shortened by trimming its proximal end. Opposite longitudinal bores are formed in each of the abutting phalanges at the joint, e.g., drilled and broached. An intramedullary support is inserted into the bore in one of the phalanges, particularly the proximal phalanx. The support is sized to protrude when fully inserted into the proximal phalanx, by substantially the same distance it will be inserted into the next distal phalanx, both end bottoming out or coming close to bottoming out in their respective bores. The distal phalange is pulled out over the protruding end of the intramedullary support, and pushed onto the protruding end. The joint capsule is sutured over the support and the incision is sutured closed. The phalanges heal with the interphalangeal joint fused.

The dimensions of the phalanges, the bores for receiving the intramedullary support and the intramedullary support itself are small and a challenge to manipulate. What is needed is an improved structure for the intramedullary support and improved techniques placing the support, that are less reliant on separating and aligning the bores in the abutting phalanges to the ends of an intramedullary support.

SUMMARY

An object of this disclosure is to reduce the extent of alignment and spacing needed to insert an end of an elongated intramedullary support manually into a bore in a bone, especially to insert a narrow, tapered or pointed head on the end of the intramedullary support into a bore in the second of two phalanges at an interphalangeal joint to be spanned by the support. This object is achieved by providing a generally conically tapered but asymmetric pointed head on the support.

It should be understood that in this context, "pointed" does not necessarily require a sharp end. A "point" encompasses sharp or rounded or other end structures, provided that the lateral span at the end or "point" is less than the lateral span across the intramedullary at points spaced longitudinally back from the end. In the context of the invention, the point also has a span at the extreme end that is less than the inside diameter of the drilled or broached bore into which the intramedullary is inserted.

In the illustrated embodiment, one end of the intramedullary is pointed and the other end is not. The pointed end or head protrudes after the intramedullary support has been set into a first of the two phalanges to be joined, for example by setting a preferably-threaded shaft of the support into a longitudinal bore in one phalanx, leaving the protruding other end to be inserted into a drilled or broached bore in the other phalanx.

The protruding pointed head advantageously is asymmetric, in that one side of the pointed head is tapered at a lower angle relative to a longitudinal axis of the support than the diametrically opposite side of the pointed head, which is more steeply angled. The pointed head is readily guided into a longitudinal bore in the second of the two phalanges.

The more steeply angled side of the pointed head can lead to a rear barb or fluke that is nearer to the end or point than at the opposite side at the lower angle, which opposite side extends to a rear fluke that is longitudinally farther from the pointed end along the pointed head structure. In certain embodiments, the radial dimension of the flukes from the longitudinal axis is substantially equal, although the flukes are at different distances from the pointed end.

An end of the intramedullary support opposite from the pointed head can be blunt or also pointed. In one arrangement the pointed head is disposed on the end of a threaded shaft dimensioned to be screwed into the bore in a first phalanx, such as a bore in the proximal phalanx at the interphalangeal joint. The support is threaded fully into the bore. Then the second phalanx at the joint (in that case the distal phalanx) is joined to the intramedullary support by pushing the second phalange onto the pointed head structure. This entails a relative movement of the pointed head structure and the phalanx relative to one another.

As a result of the tapered structure of the pointed end, and the span at the end being less than the internal diameter of the bore, the extreme end of the intramedullary support can be inserted readily, at least for a short distance, into the bore in the second phalanx, without first aligning the axis of the bore in the second phalanx to be co-linear with the axis of the intramedullary support. As the pointed end advances into the bore, one of the sides of the pointed end can slide along the rim at the entry to the bore while there is space on the diametrically opposite side.

Preferably, the intramedullary support has been preliminarily rotated prior to insertion of the pointed end, for example the support can be twisted on a threaded shaft, so as to align the less steeply tapered side of the pointed head structure to slide along the rim into the bore and along the inside of the bore into the phalanx that receives the pointed head. The longer shallower-sloped side enables the pointed head structure to be inserted up to a point at which the more steeply angled side contacts the rim of the bore.

The diametric span between the flukes on the respective steeper and shallower sides is equal to or slightly greater than the inside diameter of the bore in the phalanx that receives the pointed head structure. The intramedullary support and the bore in the second phalanx become aligned co-linearly as the pointed head structure is advanced into the second phalanx, clearing the rim. The advance continues up to the point at which the phalanges abut one another. At that point, the intramedullary is fixed in the first phalanx (e.g., the proximal one) by the thread, and is fixed in the second phalanx (e.g., the distal one) by the flukes or barbs of the pointed head structure. The second phalanx cannot be backed off of the intramedullary support because the flukes/barbs engage in the sidewalls of the bore in the second phalanx.

The foregoing objects and aspects can be realized in an intramedullary implant having opposite ends inserted into abutting bones of a joint, for correcting hammer toe and for similar arthrodesis procedures. The associated surgical procedure includes incising and dislocating the proximal interphalangeal joint, usually resecting at least one of the phalanges, and longitudinally boring or broaching both phalanges to provide a bore for receiving the implant.

A rear end of the implant is received in a bore in one of the phalanges, such as a distal bore in the proximal phalanx. A front end of the implant has an asymmetric conical pointed head shape with longitudinally and/or angularly spaced rear-facing gripping flukes or barbs. The rear end of the implant advantageously is threaded and thereby can be screwed into the bore in the proximal phalanx with the pointed end protruding distally.

The implant advantageously can be rotationally aligned so that the asymmetry of the pointed head is parallel to the sagittal plane (the asymmetry is up-and-down as opposed to lateral). The protruding pointed head is inserted into the second bore, namely into the intermediate phalanx. The pointed asymmetric shape is self-aligning, enabling entry at a relatively steep angle without first longitudinally aligning the bores in the two phalanges. The bones become aligned with further advance of the bones on the support and are longitudinally fixed in place by engagement of the rear-facing flukes in the sides of the bore in the phalanx.

BRIEF DESCRIPTION OF THE DRAWINGS

The subject matter of the disclosure is shown and described in the following discussion of exemplary embodiments, with reference to the accompanying drawings, wherein:

FIG. 1 is a phantom skeletal diagram showing a hammer toe deformity.

FIGS. 2 and 3 show steps in a surgical procedure for correcting the deformity using an embodiment of the intramedullary implant disclosed herein.

FIG. 4 shows the completed surgical repair.

FIG. 10 is an illustration of an alternative embodiment of the implant, shown from side elevation, perspective and end view.

FIG. 11 is an illustration of another alternative embodiment, shown from side elevation, perspective and end view.

DETAILED DESCRIPTION OF EXEMPLARY EMBODIMENTS

Figure 5:
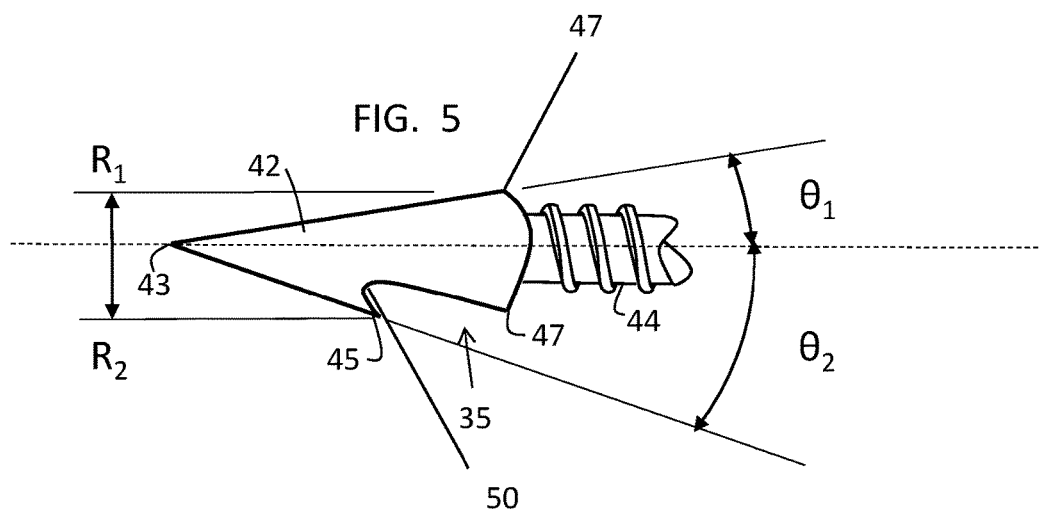
FIG. 5 is an elevation view showing the asymmetrically pointed end of the intramedullary implant with a threaded shaft of indefinite length.

FIG. 1 shows an exemplary hammer toe condition, sometimes termed a contracted toe, which can develop in the second through fifth toes and generally involves progressively increased curling of the toe with the proximal phalange 22 turned upwardly (superiorly), and the middle and distal phalanges 24, 26 turned downwardly (inferiorly). The condition can produce contact injuries such as a corn 32 on the superior side of the proximal interphalangeal joint and calluses or blisters 34 on the ball of the foot and/or at the end of the toe, which can be painful.

The hammer toe condition is corrected surgically by inserting an intramedullary support of some kind. Conventionally, a Kirschner wire (or "K-wire," not shown) is inserted from the extreme distal end of the toe. A shorter K-wire or similar support can be embedded in each of the proximal and intermediate phalanges so as to extend between the bones and immobilize the proximal interphalangeal joint with the phalanges more nearly aligned. The joint becomes ossified and fused in an arthrodesis that corrects the hammertoe deformity.

The present disclosure concerns the structure and emplacement of a particular form of intramedullary support 35 that is embedded by endwise insertion into bores 37, 39 formed in the abutting ends of the proximal and intermediate phalanges during a surgical procedure. The implant is dimensioned to engage in bores that are drilled and/or broached for receiving the implant. The structure of the implant, and the asymmetrical pointed head 42 thereof in particular, are such that the pointed head end 42 of the intramedullary support 35 can be started into the bore in the intermediate phalanx without first aligning the implant precisely to the longitudinal axis of the bore. The insertion can be commenced at a steep angle.

With continued insertion, the pointed head shape leads to the implant and the bore in the medial phalanx becoming longitudinally aligned. The head shape is barbed in a manner that permits insertion but catches if pulled back. An intermediate tang or fluke 45 (FIG. 5) is provided along the length of the pointed head 42, and preferably a further base tang or fluke 47 is provided at the back of the pointed head, i.e., spaced back from the intermediate tang or fluke 45 along the direction of insertion. This structure aligns and securely engages the intramedullary support in the bore in the bone, in a manner that prevents longitudinal retraction.

The surgical procedure commences with making a superior incision exposing the proximal interphalangeal joint, shown schematically in FIG. 2. The ligaments are parted or displaced outwardly and the joint is dislocated, exposing the normally-abutted ends of the proximal and intermediate phalanges 22, 24. It is usually desirable to resect the head of the proximal phalanx and also to plane the head of the middle phalanx, shown in FIG. 2 by dashed lines. The resecting shortens the overall length of the toe and together with planing provides facing surfaces on the ends of the proximal and middle phalanges 22, 24 where the bones abut over a considerable end surface area. An object of the surgery is to immobilize the joint with these surfaces in abutment, and after a period of healing and ossification to fuse the two phalanges 22, 24 across the proximal interphalangeal joint.

The surgeon creates bores 37, 39, shown in FIG. 3, aligned longitudinally and substantially centered in the proximal and middle phalanges, respectively. This can involve drilling a pilot hole and enlarging the pilot hole with a broach (not shown) or simply drilling a hole of the required internal diameter and length.

Preferably the length of the bores 37, 39 is only slightly more than necessary to accommodate the longitudinal dimensions of the intramedullary support 35 so that the intramedullary support 35 fully occupies the bores 37, 39 and contributes to the structural strength of the respective bones. More particularly, the pointed head 42 is dimensioned for longitudinal insertion to locate the intermediate barb or tang 45 well along the length of the bore 39 and the rear edge or tang 47 that has the greatest radial dimension, at a space from the rim or entry into the bore 39.

Preferably, the opposite end 44, which is threaded in the depicted embodiment, is inserted first into the proximal phalanx 22, e.g., being screwed into the bore 37 back to near a final position of the threaded end 44. In that position, the pointed head end 42, including its rear edge or tang 47, protrude beyond and are spaced from the head of the proximal phalanx 22. The rotational alignment of the support 35 can be adjusted to align the asymmetry of the pointed head end 42 parallel to a sagittal plane. In the embodiment shown in FIGS. 3 and 4, the steeper sloped side of the pointed head end 42 has been oriented inferiorly and the shallower sloped side is oriented superiorly.

FIG. 3 shows the bores that have been drilled and broached along the longitudinal axes of the middle and proximal phalanges, extending well into the bone tissue. The implant 35 is screwed into bore 37, leaving the pointed head end 42 protruding distally. The middle phalanx 24 is brought up to place the opening of the bore at the protruding pointed head end 42. The phalanx with bore 39 therein is pushed generally longitudinally, over the protruding pointed head end 42, until the heads of the phalanges 22, 24 are brought into abutment, i.e., contact. The tangs or flukes of the pointed head end 42 engage in the bone tissue at the inside surfaces of the bore 39 and prevent relative retraction of the implant 35 from the middle phalanx 24. The ligaments at the joint are then repaired and sutured. The external fascia is likewise sutured to close the incision.

The end result is the improved alignment of the phalanges shown in FIG. 4. The intramedullary implant 35 resists longitudinal and rotational displacement. The implant 35 immobilizes the joint, and after a period of healing, the middle and proximal phalanges fuse.

It is desirable if the intramedullary implant 35 is inserted into each of the respective phalanges by a substantial distance. It is also desirable if the implant occupies most or all of the length of the bore formed in the phalanx to receive the implant. In the illustrated example, the implant has a corrugated preferably helically-threaded end 44 received in the proximal phalanx and a conically tapered but preferably asymmetric pointed head end 42, received in the middle phalanx.

In order to maneuver the middle phalange and the proximal phalange relative to one another so as to insert the pointed end of the intramedullary implant into the bore in the middle phalange, the middle and proximal phalanges must first be spaced longitudinally, at least to clear the distance by which the implant protrudes from the proximal phalanx. The middle phalange may be pulled distally away from the proximal phalange in order to bring the opening into bore 39 up in front of the pointed end 42 of the implant 35. With conventional implants, the middle phalange would also be maneuvered at this stage to coaxially align bores 37, 39. However it is an aspect of the disclosed implant that the bores 37, 39 need not be co-linear in order to begin inserting the protruding end 42 into the bore of the middle phalanx. The bores can be oblique to one another, especially approaching with the steeper side of the pointed end resting against the edge of the bore in the phalanx that will receive the pointed end. With further advance, the particular structure of the implant facilitates the insertion process, inherently aligns the phalanges 22, 24 during insertion, and engages securely so that the phalanges are immobilized relative to one another.

Referring to FIG. 5, the threaded end 44 is complementary with bore 37 in that the outside diameter at the peaks of the threads is slightly greater than the inside diameter of the bore. The diameter of the shaft at the base of the threads is equal to or slightly less than the inside diameter of the bore. As a result, the threaded end 44 screws into the bone in a self-threading manner. The threads can be configured to engage cancellous or cortical bone within the bone canal, depending on the patient anatomy and selection of implant size.

The pointed head end 42, which is integrally formed in implant 35 with the threaded shaft 44, is generally shaped as a cone except that the cone is not symmetrical. (Also, as noted above, the point on the cone may be sharp or it may be blunt or rounded.) On one side (the lower side in FIG. 5), the conical shape leads back only to the intermediate tang or fluke 45, where the diameter of the pointed head end 42 falls off, leaving the tang or fluke 45. In the embodiment shown in FIG. 5, the tang 45 is undercut 50, such that the tang forms a rearward pointed edge as shown. The pointed head shape shown in FIG. 5 resumes a conical enlargement leading from the undercut 50 behind tang 45 to the rear edge of the pointed head end 42. The diameter falls off again at the rear edge down to the shaft or threaded end 44. This structure forms an end fluke or tang of a sort. Thus in this embodiment, the pointed head shape 42 defines a plurality of longitudinally spaced tangs or flukes at which a decrease in diameter, and optionally also an undercut 50, form edges that bite into the bone tissue adjacent to the bore 39 to impede retraction of the pointed head end 42 relative to the phalanx in which the pointed end is inserted.

It would be possible to orient the implant such that the pointed head end 42 is inserted into either of the proximal or distal bones 22, 24 of the proximal interphalangeal joint, with the threaded part engaged in the other. Inasmuch as the bones anatomically are smaller leading toward the distal end of the toe, it may be convenient and structurally secure to mount the threaded shaft 44 in the more proximal phalanx 22 and to embed the pointed head structure 42 in the more-distal intermediate phalanx 24.

Figure 6:
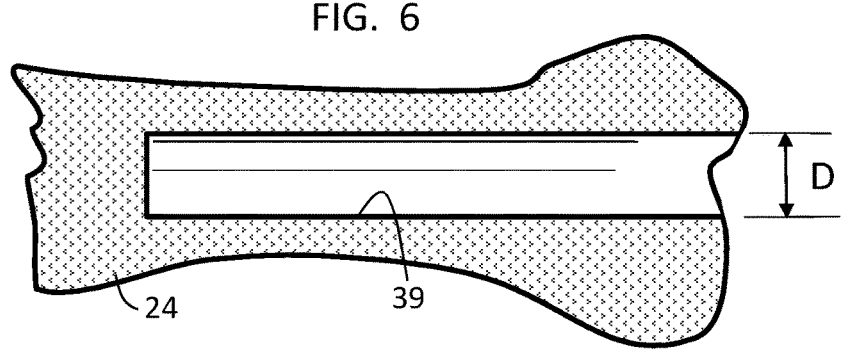
FIG. 6 is a section view showing middle phalanx, i.e., the distal member of a proximal interphalangeal joint, the middle phalanx being bored and/or broached for reception of the pointed end of FIG. 5.

Comparing FIGS. 5 and 6, the inside diameter D of the bore 39 in the phalanx 24 is slightly less than that span of radii $R_1+R_2$ measured perpendicular to the center axis (dotted line) of the implant 35 to the point of the respective barbs or tangs 45 (on one side) and 47 (on opposite sides at the end) of the pointed head structure 42. In that way, the barbs or tangs lock into the inner surface of the bore in the bone. However, the shape of the pointed head is asymmetrical. In alternative embodiments, the opposite radii $R_1$ and $R_2$ can be unequal and/or the respective angles $\theta_1$ and $\theta_2$ can be unequal.

Figure 7:
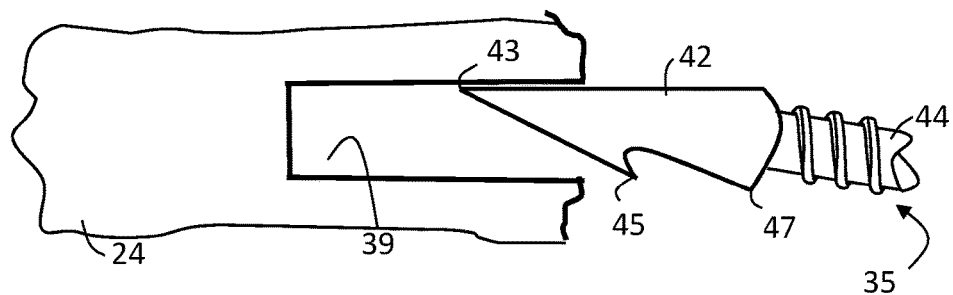
FIGS. 7 and 8 are schematic illustrations showing the change in relative alignment of the intramedullary implant and the bore in the phalanx that occurs during stages of insertion of the asymmetrical tapered structure of the implant.
Figure 8:
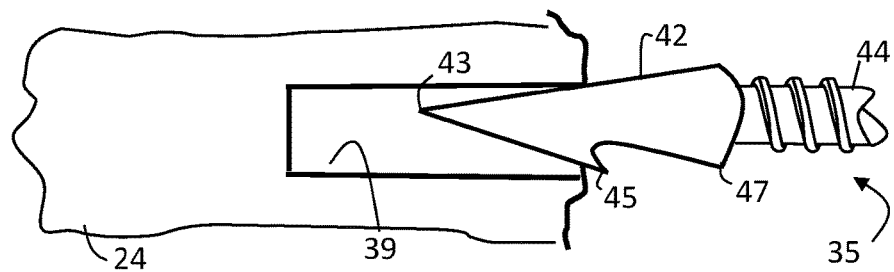

The general pointed shape of the pointed head end 42 assists in guiding the pointed head shape into the opening at the end of the bore 39 as further shown in FIGS. 7 and 8. Because the point 43 of the pointed head end 42 (which may be rounded or sharp) is smaller than the opening of the bore 39, one can commence engaging the pointed head 42 into the bore 39 without carefully lining up the center of the rim of the bore 39 with the point 43 of the pointed head shape, and without first aligning the longitudinal axes of the implant and the bore to be co-linear.

In the embodiment shown, the conical sides of pointed head 42 are straight and taper to a relatively sharp point 43. It is possible alternatively to provide a shape wherein taper is along a curve, leading to a bullet shape (not shown). It is also possible to have a conical taper but the make the point 43 more blunt than shown, e.g., rounded or truncated instead of sharp at the point 43. In another possible arrangement (not shown), the point 43 of a conical end can be truncated because the implant 35 is cannulated along the center axis for guiding a K-wire or the like, namely with a longitudinal channel emerging at point 43. In other arrangements, a conical end can be provided but made slightly oblique to the center axis of the implant. In yet another arrangement, a plurality of barbs or tangs 45 can be provided at different longitudinal points along the implant and/or as radially spaced around the center axis. Some of these alternatives are shown in the remaining drawing figures.

Figure 9:
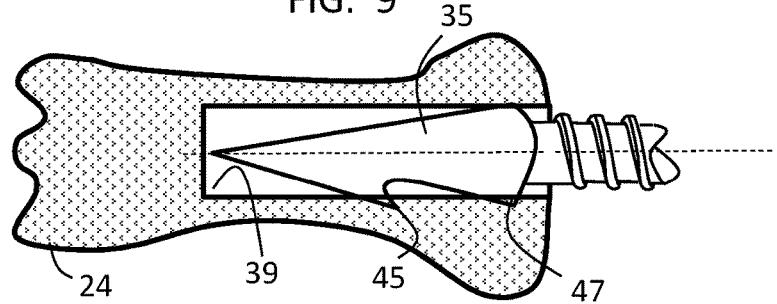
FIG. 9 is a section view of the intramedullary implant in final position in the phalanx.

As illustrated in FIGS. 7 and 8, an asymmetrical and/or oblique conical taper at the point is useful to interact with the edges and surfaces of the bore 39 into which the pointed head 42 is inserted. Whether sharp or rounded, the end of the pointed end has a span less than the internal diameter of the bore, such that insertion can be commenced by generally moving the end into the larger bore. As the pointed head 42 is advanced into the bore 39, the pointed head 42 can be guided along the rim of the entry into the bore 39, on either the steeply or shallowly tapered sides (or along a lateral side). By selectively aligning the pointed head 42 rotationally when screwing the threaded shaft into the proximal phalange 22, the asymmetry in slope can be placed parallel to the sagittal plane. That is, one can selectively place the steeper or shallower slope on the superior or inferior side of the implant 35. This is helpful to assist in guiding the pointed head 42 into the bore 39 in the middle phalange 24 from a starting position wherein the phalanges are not already aligned, e.g., curling obliquely in the plantar direction. In FIG. 7, upon starting insertion (which might involve moving the point 43 into the bone 24, or moving the bore 39 in bone 24 over the point 43, or both), the pointed head structure 42 is guided along a shallower side against the inside of the rim for a length of penetration up to the contact of the opposite side against the opposite edge of the rim. With continued insertion, the pointed head end 42 and the implant 35 as a whole align co-linearly with the bore 39. The outside diameter of the pointed head end 42 slightly exceeds the inside diameter of the bore 39, specifically at the tangs 45, 47. With continued insertion, first the intermediate tang 45 and eventually plural tangs 45, 47, engage in the bone tissue, as shown in FIG. 9. Any force tending to retract the pointed end 42 from the bone cause the points of the tangs 45, 47 to dig into the bone tissue to impede retraction in the manner of a barb. Furthermore, the asymmetry in the taper of the pointed end 42 on opposite sides prevents relative rotation of the pointed end 42 in the bone. The implant 35 remains in its final position shown in FIG. 9 and also in FIG. 4.

As described, the bones of the proximal interphalangeal joint in this example, are immobilized by an intramedullary implant 35 including an implant body with an anchoring structure along a longitudinal axis, namely the tapered/pointed end 42. The implant 35 is configured for insertion in one direction into a bore 39 in a bone 24 for gripping the sides of the bore, and resists retraction of the intramedullary implant 35 from the bone in a direction opposite from the direction of insertion.

The intramedullary implant has a pointed head 42 having a point 43 at a leading end of the implant 35 and surfaces tapering outward and rearward at angles $\theta_1$ and $\theta_2$ from the point, to respective gripping flukes 45, 47 spaced back from the leading end. Two or more surfaces that taper outwardly and rearwardly can be two diametrically opposite surfaces or plural surfaces angularly spaced around an axis, at different angles and/or to different radial distances. Two diametrically opposite surfaces taper outward and rearward at different angles ($\theta_1 \neq \theta_2$) and/or can progress to different radial spans ($R_1 \neq R_2$) or both as shown in FIG. 5. Additional or otherwise configured asymmetrically tapered surfaces are shown in alternative embodiments depicted in FIGS. 10 and 11. In each of the depicted embodiments, a pointed end 42 is provided opposite from a shaft that is optionally threaded. The pointed end is asymmetric and carries a plurality of gripping tangs or flukes 45, 47, 55 at different radial spans and/or at longitudinally spaced locations leading rearward from a leading end point 43 in the direction of insertion and/or angularly spaced around the pointed end.

In FIGS. 10 and 11, intermediate flukes 55 are provided at different angular positions around the circumference of pointed heads with different shapes. As in the previous embodiment, FIG. 10 includes longitudinally spaced tangs 55, 47. In FIG. 11, there are surfaces at unequal angles $\theta_1$ and $\theta_2$ but the flukes 55 in this embodiment are the sole barbed structure. Gripping flukes 45, 47, 55 can be provided closer to the leading end and also farther back. FIGS. 10 and 11 employ forwardly placed gripping flukes 55. The gripping flukes that are closer to the point 43 (flukes 45 or 55) have a greater angle of outward and rearward taper than the flukes 47 that are farther from the point 43 at the leading end, and may define the rear edge of the pointed end 42.

As discussed, the pointed head shape 42 can be configured with a difference in the radial distance from the center axis to the fluke or barbed edge ($R_1 \# R_2$). In each of these examples, the barbed edge or fluke is defined by an undercut or drop-off 50 in the diametrical span at the respective gripping flukes, immediately behind such flukes along the longitudinal direction of insertion. Additionally, the diametrical span of the pointed head 42, generally the distance between opposite surfaces of which at least one ends at a fluke or barb 45, 47, 55, is greater than an internal diameter of the bore 39. Thus the gripping flukes engage in the sidewalls of the bore 39 to prevent retraction. In the case of an undercut or drop-off 50 behind such flukes, the barbs are oriented rearward and thus are disposed to bite more deeply into the bone tissue of the bore 39 if force is exerted in a direction tending to retract the implant from the bore 39.

Referring to FIG. 7, the internal diameter of the bore 39 advantageously is approximately equal or slightly larger than the span between point of the fluke 45 and the shallower sloped opposite side of the pointed end, measured perpendicular to the axis of the implant. In this way, as the pointed end commences entry into the bore 39 while the pointed end is oblique to the axis of the bore 39, the fluke passes into the bore without interference. As the insertion continues, as shown in FIG. 8, and the center axis of the implant is brought into alignment with the axis of the bore, that span becomes perpendicular to the axis of bore 39, and the fluke is urged to dig into the inside wall of the bore because the perpendicular span between point of the fluke and the opposite side wall, measured perpendicular to the axis of the implant, is then greater than the inside diameter of bore 39.

The implant 35 as described advantageously forms at least part of a prosthesis for arthrodesis of an inter-phalangeal joint to correct hammer toe deformity and is configured for engagement of both phalanges 22, 24 abutting at said joint. Advantageously the proximal end 44 of the implant 35 opposite from the pointed head 42 is threaded such that the implant is twisted (rotated) to screw the proximal end 44 into the proximal phalanx whereas the pointed head 42 engages in the middle phalanx. The thread allows the implant 35 to be rotated such that the shallower or steeper side of an asymmetrical embodiment of the pointed head 42 is oriented in a superior or inferior direction. Thus the implant 35 can be oriented to commence insertion into the bore 39 in the intermediate phalange 24 without first aligning the pointed end 42 or the implant 35 as a whole coaxially with the bore 39.

The associated method for surgical repair of an interphalangeal joint or the like thus includes forming a bore 39 along a longitudinal bore axis in at least one phalanx 24 at the joint for receiving an intramedullary support 35 including an implant body with pointed anchor end 42 facing along a longitudinal axis, wherein the anchor end has a pointed head 42 having a point 43 at a leading end and diametrically opposite surfaces tapering outward and rearward at different angles, ending in respective gripping flukes 45, 47, 55. The longitudinal axis of the intramedullary support 35 advantageously can be aligned oblique to the longitudinal bore axis when moving the leading end of the intramedullary support into the bore (see FIG. 7).

Insertion is accomplished while guiding one of the diametrically opposite surfaces along an edge of the bore. The pointed or anchor end 42 of the intramedullary support 35 is advanced into the bore 39, which is dimensioned such that one or more other surfaces engages the edges and inner surfaces of the bore. Advancing the two phalanges 22, 24 of the joint into abutment brings the longitudinal axis of the intramedullary support 35 into alignment with the bore axes (see FIG. 9). At a full insertion position determined by abutment of the bones, the anchor end resides at a final position in the bore, preferably adjacent to an end of the bore. The gripping flukes 45, 47, 55 engage in the bone along the walls of the bore 39 and prevent retraction.

Advantageously the proximal part of the implant has a threaded shaft enabling the implant to be screwed into a bore 37 in the proximal phalanx. By finally aligning the asymmetry of the partly conical pointed head 42 parallel to the sagittal plane, initial insertion of the pointed head 42 can be guided along the slope on one side of the pointed head 42. The asymmetric shape is self-aligning, enabling entry without substantial requirements for longitudinal alignment, but with continued advance serving to align the bones and the implant such that the bones can fuse while the implant 35 holds the bones stationary and in abutment.

In the exemplary embodiments, the implant has a pointed end shape on one end and a shaft on the other end that is preferably but not necessarily threaded. It is also possible to provide pointed ends facing in both directions to be received in the abutting bones.

The associated method can include incising and dislocating the proximal interphalangeal joint, resecting at least one of the phalanges and boring and broaching both phalanges for insertion of the intramedullary implant 35 as described. After a period of healing, the interphalangeal joint is fused at a more nearly correct anatomical alignment of the phalanges parallel to the horizontal or plantar plane.

The invention has been disclosed in connection with certain embodiments having attributes that are advantageous for the reasons described. These attributes can be realized together or individually and with other features without departing from the invention. Reference should be made to the appended claims as opposed to the foregoing description of embodiments and examples, in order to assess the scope of the invention claimed.

What is claimed is:

1. An intramedullary implant, comprising;
   an implant body including an anchor end and a shaft, the shaft defining a longitudinal axis, the anchor end being configured for insertion in one direction into a bore in a bone for gripping sides of the bore, and resisting retraction of the intramedullary implant from the bone in an opposite direction;
   wherein the anchor end is a single conical body having a surface shaped as a portion of a single cone, the surface tapering outward and rearward from an apex point of the single cone, where the apex point is disposed along the longitudinal axis of the shaft, the single cone having an undercut on a single side of the longitudinal axis, the undercut extending only partially around the single cone so the cone is not rotationally symmetrical about an axis thereof, the surface extending to a first gripping fluke formed by a barb generated by the undercut and a second gripping fluke formed by a rear edge of the single conical body spaced back from the apex;
   wherein said first and second gripping flukes are longitudinally spaced from one another relative to the longitudinal axis and taper outward and rearward, and
   wherein the conical body defines a central axis passing through the apex point, the central axis disposed at an oblique angle with respect to the longitudinal axis such that a distance from the longitudinal axis to a first point on the surface is greater than a distance from the longitudinal axis to a second point on the surface which is diametrically opposed from and longitudinally aligned with the first point with respect to the longitudinal axis.

2. The implant of claim 1, wherein the gripping fluke that is closer to the apex point has a greater angle of outward and rearward taper than the gripping fluke that is farther from the apex point.

3. The implant of claim 1, wherein a diametrical span between locations on the first and second gripping flukes which are located on diametrically opposite portions of the surface is configured to be greater than an internal diameter of the bore, whereby the gripping flukes are configured to engage opposite sidewalls of the bore.

4. The implant of claim 1, wherein the implant forms at least part of a prosthesis for arthrodesis of an inter-phalangeal joint and is configured for engagement of both phalanges abutting at said joint.

5. The implant of claim 1, wherein the shaft is threaded.

6. A method for surgical repair of an interphalangeal joint, comprising:
   forming a bore along a longitudinal bore axis in at least one phalanx at the joint;
   providing an intramedullary support including an implant body including an anchor end and a shaft, the shaft defining a longitudinal axis, wherein the anchor end is a single conical body having a surface shaped as a portion of a single cone, the surface tapering outward and rearward from an apex point of the single cone, where the apex point is disposed along the longitudinal axis of the shaft, the single cone having an undercut on a single side of the longitudinal axis of the shaft, the undercut extending only partially around the single cone so the cone is not rotationally symmetrical about an axis thereof, the surface extending to a first gripping fluke formed by a barb generated by the undercut and a second gripping fluke formed by a rear edge of the single conical body spaced back from the apex, wherein said first and second gripping flukes are longitudinally spaced from one another relative to the longitudinal axis and taper outward and rearward, and wherein the conical body defines a central axis passing through the apex point, the central axis disposed at an oblique angle with respect to the longitudinal axis of the shaft such that a distance from the longitudinal axis of the shaft to a first point on the surface is greater than a distance from the longitudinal axis of the shaft to a second point on the surface which is diametrically opposed from and longitudinally aligned with the first point with respect to the longitudinal axis of the shaft;
   orienting the implant body so the longitudinal axis of the shaft is oblique to the longitudinal bore axis and moving the apex point of the intramedullary support into the bore;
   advancing the anchor end into the bore, whereby the anchor end brings the longitudinal axis of the shaft into alignment with the bore axis; and
   continuing to advance the anchor end into the bore to an end position at which the gripping flukes engage the bore to prevent retraction.

7. The method of claim 6, further comprising inserting the shaft into a second phalanx and rotationally aligning the intramedullary support such that the central axis is parallel to a sagittal plane prior to moving the anchor end into the bore.

8. The method of claim 7, wherein the shaft is threaded, wherein said inserting of the shaft comprises screwing the intramedullary support into the second phalanx.

9. The method of claim 8, wherein the anchor end protrudes beyond the second phalanx after screwing the intramedullary support into the second phalanx.

10. The method of claim 9, further comprising rotating the shaft to selectively place the surface of the anchor end in position for guiding along the edge of the bore.

11. An intramedullary implant, comprising;
    an implant body having a longitudinal axis; and
    an anchor along the longitudinal axis, the anchor being configured for insertion in one direction into a bore in a bone for gripping sides of the bore, and resisting retraction of the intramedullary implant from the bone in an opposite direction;

wherein the anchor has:

an anchor head at a leading end of the implant body, the anchor having a point located along the longitudinal axis;

three convex surfaces tapering outward and rearward from the point at spaced angles around the anchor head, to respective first gripping flukes spaced back from the leading end, the gripping flukes defined by undercuts in the three convex surfaces, at least two of the undercuts being located at respectively different distances along the longitudinal axis relative to the point, the anchor head having three concave surfaces angularly spaced between respective ones of the three convex surfaces; and three second gripping flukes longitudinally spaced from the first gripping flukes relative to the longitudinal axis, the three second gripping flukes angularly spaced from the three first gripping flukes.

12. The intramedullary implant of claim 11, wherein the convex surfaces are arranged at respectively different angles from the longitudinal axis of the implant body.

* * * * *